United States Patent [19]
Wilkinson

[11] 3,939,219
[45] Feb. 17, 1976

[54] HYROGENATION OF UNSATURATED COMPOUNDS
[75] Inventor: Geoffrey Wilkinson, London, England
[73] Assignee: Johnson, Matthey & Co., Limited, London, England
[22] Filed: Feb. 6, 1973
[21] Appl. No.: 330,106
[30] Foreign Application Priority Data
July 14, 1969 United Kingdom........... 35249/69

Related U.S. Application Data
[63] Continuation-in-part of Ser. No. 53,031, July 7, 1970, Pat. No. 3,725,305.

[52] U.S. Cl. ..... 260/666 P; 260/485 R; 260/488 K; 260/532; 260/537 R; 260/612 D; 260/604 HF; 260/641; 260/642 R; 260/666 A; 260/677 H; 260/683 R; 260/683 D; 260/683.2; 260/683.9; 260/690
[51] Int. Cl.$^2$... C07C 5/02; C07C 5/04; C07C 5/06; C07C 5/08
[58] Field of Search ......... 260/683.9, 485 R, 666 P, 260/666 A, 683 R, 677 H, 690

[56] References Cited
FOREIGN PATENTS OR APPLICATIONS
2,034,908  1/1971  Germany
2,034,909  1/1971  Germany Primary Examiner—Anton H. Sutto
Assistant Examiner—Jane S. Myers
Attorney, Agent, or Firm—Cushman, Darby & Cushman

[57] ABSTRACT
The invention described in the specification concerns a process for the homogeneous liquid phase hydrogenation of an olefinically or acetylenically unsaturated organic compound to produce a compound having a lower degree of unsaturation by contact of the said organic compound with molecular hydrogen in the presence of a catalyst solution containing a catalytically effective amount of a cation selected from the group consisting of:

$M^{n+}{}_2$; $M_2(OCOR)^{n+}{}_{4-n}$; $M_2(OCSR)^{n+}{}_{4-n}$ and $M_2(SCSR)^{n+}{}_{4-n}$ the said solution being prepared by the addition of strong acid to a solution of a compound selected from the group consisting of:

$M_2(OCOR)_4$;   $M_2(OCOR)_4L$;   $M_2(OCOR)_4L_2$;
$M_2(OCSR)_4$; $M_2(OCSR)_4L$;
$M_2(OCSR)_4L_2$; $M_2(SCSR)_4$; $M_2(SCSR)_4L$ and $M_2(SCSR)_4L_2$ where M is a metal selected from the group consisting of Mo, Cr, Cu, Re and metals of the platinum group;
R is selected from the group consisting of alkyl and aryl;
L is ligand selected from the group consisting of $H_2O$, $CH_3OH$, $C_2H_5OH$, CO, pyridine, $Cl^-$ and $Br^-$;
n is a positive integer from 1 to 4;
(OCOR) represents a carboxylate radical;
(OCSR) represents a thiocarboxylate radical, and
(SCSR) represents a dithiocarboxylate radical, and the said solution including a stabilising amount of a donor ligand selected from the group consisting of pyridine, quinoline, dimethylaniline, dibutyl sulphide, dimethyl sulphide, triphenyl phosphine oxide, phenyl isocyanide, acetonitrile, phosphorus tri-isocyanate, phosphorus tri-isothiocyanate, stannous halide, germanium (II) halide and a ligand having the formula $MR'_3$ where M is selected from the group consisting of phosphorus, arsenic and antimony and R' is selected from the group consisting of alkyl, aryl and aryloxy radicals.

22 Claims, No Drawings

HYDROGENATION OF UNSATURATED COMPOUNDS

This application is a continuation-in-part of Ser. No. 53031 filed July 7, 1970, now issued as U.S. Pat. No. 3,725,305. Said patent describes and claims catalyst compositions containing a catalytically effective amount of a cation selected from the group consisting of:

$M_2^{n+}$
$M_2(OCOR)_{4-n}^{n+}$
$M_2(OCSR)_{4-n}^{n+}$
and
$M_2(SCSR)_{4-n}^{n+}$ where M is a metal selected from the group consisting of Mo, Cr, Cu, Re and metals of the platinum group;
  R is selected from the group consisting of alkyl and aryl;
  n is a positive integer from 1 to 4
  (OCOR) represents a carboxylate radical;
  (OCSR) represents a thiocarboxylate radical, and
  (SCSR) represents a dithiocarboxylate radical.

According to one aspect of the present invention there is provided a process for the homogeneous liquid phase hydrogenation of an olefinically or acetylenically unsaturated organic compound to produce a compound having a lower degree of unsaturation by contact of the said organic compound with molecular hydrogen in the presence of a catalyst solution containing a catalytically effective amount of a cation selected from the group consisting of:

$M_2^{n+}$
$M_2(OCOR)_{4-n}^{n+}$
$M_2(OCSR)_{4-n}^{n+}$
and
$M_2(SCSR)_{4-n}^{n+}$ the said solution being prepared by the addition of strong acid to a solution of a compound selected from the group consisting of
  $M_2(OCOR)_4$
  $M_2(OCOR)_4L$
  $M_2(OCOR)_4L_2$
  $M_2(OCSR)_4$
  $M_2(OCSR)_4L$
  $M_2(OCSR)_4L_2$
  $M_2(SCSR)_4$
  $M_2(SCSR)_4L$
and
  $M_2(SCSR)_4L_2$ where M is a metal selected from the group consisting of Mo, Cr, Cu, Re and metals of the platinum group;
  R is selected from the group consisting of alkyl and aryl;
  L is a ligand selected from the group consisting of $H_2O$, $CH_3OH$, $C_2H_5OH$, CO, pyridine, $Cl^-$ and $Br^-$;
  n is a positive integer from 1 to 4;
  (OCOR) represents a carboxylate radical;
  (OCSR) represents a thiocarboxylate radical, and
  (SCSR) represents a dithiocarboxylate radical, and
  the said solution including a stabilising amount of a donor ligand selected from the group consisting of pyridine, quinoline, dimethylaniline, dibutyl sulphide, dimethyl sulphoxide, triphenyl phosphine oxide, phenyl isocyanide, acetonitrile, phosphorus tri-isocyanate, phosphorus tri-isothiocyanate, stannous halide, germanium (II) halide and a ligand having the formula $MR_3'$ where M is selected from the group consisting of phosphorus, arsenic and antimony and R' is selected from the group consisting of alkyl, aryl and aryloxy radicals.

The cationic species produced are generally, but not necessarily binuclear. When the oxidation state of the metal is formally II a binuclear metallic cation may have a charge of +4. In one example, the reaction proceeds as follows:
  $Rh_2(OCOCH_3)_4 + 4H^+ \rightarrow Rh_2^{4+} + 4CH_3COOH$ Partial displacement of the carboxylate or substituted carboxylate, instead of full displacement may take place; for example:
  $Rh_2(OCOCH_3)_4 + H^+ \rightarrow Rh_2(OCOOH_3)_3^+ + CH_3COOH$ In this case the cationic species with one positive charge also shows good catalytic activity.

Some examples of the catalyst precursor compounds which produce active species according to this invention on protonation are:

$Rh_2(OCOR)_4$;    $Rh_2(OCSR)_4$;    $Rh_2(SCSR)_4$;
$Mo_2(OCOR)_4$;    $Mo_2(OCSR)_4$;    $Mo_2(SCSR)_4$;
$Cr_2(OCOR)_4$;    $Cr_2(OCSR)_4$;    $Cr_2(SCSR)_4$;
$Ru_2(OCOR)_4Cl$;  $Ru_2(OCSR)_4Cl$;  $Ru_2(SCSR)_4Cl$;
$Ru_2(OCOR)_4$;    $Ru_2(OCSR)_4$;    $Ru_2(SCSR)_4$;
$Cu_2(OCOR)_4$;    $Cu_2(OCSR)_4$;    $Cu_2(SCSR)_4$;
$Re_2(OCOR)_4Cl_2$; $Re_2(OCSR)_4Cl_2$; $Re_2(SCSR)_4Cl_2$;
$Re_2(OCOR)_4(CO)_2$; $Re_2(OCSR)_4(CO)_2$; $Re_2(SCSR)_4(CO)_2$;
$Re_2(OCOR)_4$;    $Re_2(OCSR)_4$;    $Re_2(SCSR)_4$;
$Ir_2(OCOR)_4$;    $Ir_2(OCSR)_4$;    $Ir_2(SCSR)_4$.

Especially effective are the tetracetate compounds, i.e. those of the first column, when R = $CH_3$.

Oxidation states other than 2 can be involved. For example the ruthenium complex $Ru_2(OCOR)_4Cl$ contains formally Ru(II) and Ru(III) (see example 3 below). The rhenium complex $Re_2(OCOR)_4Cl_2$ contains formally, Re(III).

The strong acid referred to above may, for example, be fluoroboric acid, perchloric acid, fluorosulphuric acid, trifluoromethane sulphuric acid, sulphuric acid or hydrofluoric acid; hydrofluoric acid may be used alone or in combination with a Lewis acid such as $SbF_5$, $SiF_4$ or $BF_3$.

As mentioned in the parent application the catalyst composition contains the species:
  $M_2^{n+}$;
  $M_2(OCOR)_{4-n}^{n+}$;
  $M_2(OCSR)_{4-n}^{n+}$,
or
  $M_2(SCSR)_{4-n}^{n+}$, and for the purpose of brevity and clarity, additional neutral or negative ligands indicated above, such as $H_2O$, are not always indicated as being present in cationic species in this specification. This would not, of course, be taken to mean that such species are definitely excluded.

The cationic species may be exchanged on to cation exchange resins or similar exchange solids such as zeolites, phosphates such as sodium hexametaphosphate, i.e. "Calgon" etc. They may also be adsorbed on to activated charcoal and other similar solids.

The solid material is preferably a cation exchange resin such as sulphonated polystyrene in the form of porous resin beads.

If, when carrying out the invention, the cationic species liberated by protonation is adsorbed on to a cation exchange resin (or a similar exchange material as described above), the resulting material is useful, for example, as a heterogeneous catalyst for hydrogenation, carbonylation, hydroformylation and the related reactions of olefine or other organic materials either in the gas or liquid phase, or in suspension solution (with beads of ion-exchange resin, for example). Ambient or elevated temperatures may be used.

Such solid state catalysts will also promote for example:
a. the carbonylation of methanol to acetic acid,
b. the carbonylation of amines to amides,
c. the isomerisation and disproportionation of alkenes, alkapolyenes and related compounds,
and
d. the hydrosilation of alkenes.

Solutions of the metal carboxylate, thio or dithiocarboxylate in methanol (or a similarly polar solvent) in the presence of excess protonating acid (e.g. $HBF_4$) and subsequent addition of additional donor ligand for stabilisation purposes are active catalysts for example for the hydrogenation of alkenes of all types including conjugated polyenes, acetylenes generally ($R'C \equiv CR$ where R and R' may also be H) and other unsaturated substrates containing carbon — carbon double and triple bonds such as carboxylic acids, ketones, ethers, steroids, esters and alcohols, for example at 25°C and atmospheric pressure.

Some suitable donor ligands for stabilisation purposes are:

$R_1R_2R_3P$
$R_1R_2R_3As$
$R_1R_2R_3Sb$
$R_1R_2S$
$R_1R_2R_3N$ in which $R_1$, $R_2$ and $R_3$ may be the same or different and may be hydrogen, aryl or alkyl substituents. Heterocyclic N-bases such as pyridine, dipyridyl, etc. are also suitable donor ligands.

Suitable organo-phosphorus, organo-arsenic and organo-antimony ligands which may comprise part of this invention are those consisting of tertiary organo-phosphorus, organo-arsenic, and organo-antimony compounds in which the phosphorus, arsenic, and antimony atoms are trivalent and are referred to in this specification as phosphines, arsines and stibines, respectively. In the group of suitable ligands containing the trivalent phosphorus, arsenic, and antimony atoms employed in the catalyst of this invention, the individual phosphorus, arsenic, and antimony atom has one available or unshared pair of electrons. An aryl or aryloxy derivative of trivalent phosphorus, arsenic, and antimony with the foregoing electronic configuration is, therefore, a suitable ligand for the catalyst of this invention. Such radicals, therefore, are bonded to the phosphorus, arsenic, and antimony atoms, and the radicals are selected from the group consisting of aryl and aryloxy groups. However, the preferred phosphine, arsine, and stibine ligands are those consisting of at least one, but preferably three aryl-and/or aryloxy-groups as the organic moieties. For example, preferred ligands are illustrated by the following structural formula and examples:

$MR_3'$ where M is P, As, Sb, and R' = phenyl ($C_6H_5$—), phenoxy ($C_6H_5O$—) toly [$CH_3(C_6H_4)$—], xylyl ($CH_3C_6H_3CH_3$) e.g. $P(C_6H_5)_3$ $P(C_6H_5O)_3$, $As(C_6H_5)_3$, $Sb(C_6H_5)_3$, $P[CH_3(C_6H_4)]_3$. However, a more preferred group of ligands includes the triphenylphosphines, triphenylphosphites, triphenylarsines and triphenylarsenites. The important component is the aryl or aryloxy group, e.g. the phenyl or phenoxy radical. However, the molecule may also contain some aryl groups in addition to the aryloxy radical.

A preferred group of ligands associated with the organic phosphorus, arsenic, and antimony derivatives has aryl and aryloxy radicals having from 6 to 18 carbon atoms.

Generally speaking, suitable donor ligands for stabilisation purposes are:
a. an organic isocyanide;
b. an organic compound having in the molecule an atom of an element selected from groups 5B or 6B of the Periodic Table, that is, usually a N, P, As, Sb, O, S or Se atom, such atom being in such a valency state that it possesses a lone pair of electrons, or
c. a stannous or germanium (II) halide.

Preferred ligands within the definition of categories (a) and (b) include: tertiary amines, phosphines, arsines and stibines; organic nitriles and isocyanides; sulphoxides, phosphine oxides, dialkyl sulphides and mercaptans.

For example, there may be employed pyridine, quinoline or dimethylaniline; though less basic compounds are preferred, for example, tributyl or triphenyl phosphine, trimethyl phosphite, ethyl diphenyl phosphine, dimethylphenyl arsine, triphenyl arsine or stibine, dibutyl sulphide, dimethyl sulphoxide, triphenyl phosphine oxide, phenyl isocyanide or acetonitrile. Also to be treated as organic compounds for present purposes are ligands within category (b) such as phosphorus tri-isocyanate and phosphorus tri-isothio cyanate.

Such donor ligands for stabilisation purposes are often described as biphyllic ligands. By "biphyllic ligand" is meant a compound having an element with a pair of electrons capable of forming a co-ordinate bond with a metal atom and simultaneously having the ability to accept electrons from the metal, thereby providing additional stability to the resulting complex. The term biphyllic ligand has been defined by R. G. Pearson — see J.A.C.S. 82 787 (1960). The carbon monoxide molecule is an example of a suitable biphyllic ligand. The biphyllic ligand may also be a polydentate compound, co-ordinating at more than one position to the central metal atom or ion.

Catalysts according to this invention have an advantage over other homogeneous catalysts such as $RhCl(PPh_3)_3$, $RhH(CO)(P Ph_3)_3$ or $RuH(Cl) (P Ph_3)_3$ in that they are completely and readily soluble in polar solvents such as methanol, olefinic substrates to be hydrogenated which are insoluble or sparingly soluble or benzene-alcohol mixtures can now be hydrogenated in a wholly polar medium.

Catalyst solutions according to this invention will also catalyse the hydroformylation reactions of alkenes, alkynes and other unsaturated materials with C=C and $C \equiv C$ bonds. These reactions may be carried out using carbon monoxide and hydrogen mixtures (which can be 1:1 or other ratios) at temperatures from 15° – 200°C or above, and at pressures from 1 atm upwards.

Catalyst solutions according to this invention will also isomerise alkenes and other unsaturated substances by causing double bond migration as well as cis ⇌ trans isomerisation.

Solutions according to this invention will catalyse the formation of acetic acid from methanol and carbon monoxide under mild conditions (e.g. 100°C and under 50 atm. pressure). In this case the presence of a halogen promoter is desirable and methyl iodide has been found to be a satisfactory one in this case.

The foregoing are only some of the chemical reactions for which the compositions according to the invention can act as catalysts.

The invention will now be described in more detail with reference to the following examples.

EXAMPLE 1

Commercial rhodium trichloride trihydrate (5.0 g) and sodium acetate trihydrate (10.0 g) in glacial acetic acid (100 ml) and absolute ethanol (100 ml) were gently refluxed under nitrogen for an hour.

The initial red solution rapidly became green and a green solid was deposited. After cooling to room temperature the green solid was collected by filtration through a Büchner or sintered filter funnel.

The crude product was dissolved in boiling methanol (ca. 600 ml) and filtered; after concentration to about 400 ml the solution was kept in a refrigerator overnight. After collection of the crystals, the solution was concentrated and cooled to yield a further small amount of the methanol adduct $[Rh(OCOCH_3)_2]_2.2CH_3OH$.

The blue green adduct was heated in vacuum at 45° for 20 hours to yield emerald green crystals of $[Rh(OCOCH_3)_2]_2$. A check on the removal of methanol was made periodically by taking an infrared spectrum.

Properties

The copper acetate type structure has been shown by X-ray diffraction. The complex is diamagnetic; it is only slightly soluble in water, methanol, acetone, etc., giving green solutions. Adducts with a variety of ligands have been characterised.

The infrared spectrum has bands at 1580s, 1425s, 1355m in nujol mulls (in hexachlorobutadiene 1445s, 1415s, 1350m) due to carboxylate frequencies, as well as $CH_3$ absorption.

The addition of a stoichiometric amount of aqueous concentrated fluoroboric acid to a methanol or water suspension of the acetate of 60° gives a clear green solution after about 12 hours which contains the ion $Rh_2^{4+}$.

The green solution of $Rh_2^{4+}$ in methanol normally requires the presence of other stabilising donor ligands, as described above in order to exhibit any substantial catalytic activity.

On the addition of a stabilising donor ligand such as triphenyl phosphine, for example, to the green solution an active catalyst for the homogeneous hydrogenation of alkenes and alkynes is obtained. Comparative rates of reaction under standard conditions are given in Example 2.

The catalyst solution in the following examples was made up as required from a stock solution of $Rh_2^{4+}$ in methanol and the phosphine was added, via a syringe, to the reaction flask. The apparatus and general techniques used have been described previously in J. Chem. Soc. (A) 1966 p.1711.

Catalytic activity of the protonated solution is highest with a Rh : P $Ph_3$ ratio of 1:2. The activity appears to be poisoned by oxygen and carbon monoxide, and this effect cannot be reversed by sweeping with hydrogen.

The solutions with Rh:P $Ph_3$ of 1:2 are normally red, but on addition of certain unsaturated substances, notably unsaturated carboxylic acids and alcohols, a change in colour to yellow-green occurs, presumably due to the formation of complexes, possibly of Rh (II).

The methanolic solutions of $Rh_2^{4+}$ react with many donor ligands, e.g. $R_2NCS_2^-$, amines, etc., to give a wide variety of complexes. With oxygen donors such as dimethyl sulphoxide, hexamethyl phosphoramide, alcohols, ketones and esters, the solutions stay green and presumably these substances are merely solvating the ion.

Where the preparation of a carboxylate compound complex or ionic species is described in this specification, the corresponding thio- and dithio-analogues may be assumed to be prepared similarly, with appropriate modifications.

EXAMPLE 2

Rhodium system

The activity of protonated Rh solution prepared as in Example 1 for the hydrogenation of various substrates is given below:

( [Rh] = 2.50 mM, [acetylene or olefin] = 1.0 M, $P'_{H_2}$ = 45 cm, solvent : methanol,
Reaction temperature 25°, [$PPh_3$] = 5.0 mM)

| Substrate | Rate ml/min | Substrate | Rate ml/min |
|---|---|---|---|
| Hex-1-ene | 10.9 | n-Hex-1-yne | 34.2 |
| cis and trans HeX-2-ene | 3.3 | 3 methyl butyn 1-ol-3 | 44.8 |
| cis Hept-2-ene | 2.2 | Propargyl alcohol | 17.6<sup>a</sup> |
| Cyclohexene | 1.1 | Acetylene dicarboxylic acid | <0.1<sup>a</sup> |
| 1,5 Hexadiene | 36.6 | | |
| Allyphenyl ether | 14.1 | Cyclo octa-1,5 diene | 0.6<sup>b</sup> |
| Diethyl maleate | 4.8 | | |
| Maleic acid | 0.2 | | |

<sup>a</sup>[$PPh_3$] = 20.0 mM
<sup>b</sup>$P_{H_2}$ = 50 mm

EXAMPLE 3

Ruthenium system

The activity of protonated $Ru_2(OCOCH_3)_4Cl$ for the hydrogenation of various substrates is given below:

( [Ru] = 2.50 mM, [acetylene or olefin] = 1.0.M, $P'_{H_2}$ = 45 cm, solvent or methanol
Reaction temperature 25°, [$PPh_3$] = 5.0 mM)

| Substrate | Rate ml/min | Substrate | Rate ml/min |
|---|---|---|---|
| Hex-1-ene | 30.5 | 3 methyl but-1-yne-3-ol | 14.1 |
| cis,trans Hex-2-ene | 0.5 | | |
| 1,5 Hexadiene | 46.2 | | |
| Allyl phenyl ether | 1.3 * | | |

\* $P'_{H_2}$ = 50 cm.

EXAMPLE 3A

The activity of a ruthenium catalyst made by the protonation of $Ru_2(OCOMe)_4.2PPH_3$ under hydrogen is given below:

( [Ru] = 2.50 mM, [acetylene or olefin] = 1.0M, $P_{H_2}$ = 45 cm, reaction temperature = 30°C, $PPh_3$ = 5.0 mM, solvent = methanol

| Substrate | Rate ml/min |
|---|---|
| Hex-1-yne | 0.4<sup>a</sup> |
| Hex-1-ene | 41.8 |
| Cyclo octa-1,5 - diene | 48.7 |

<sup>a</sup>$P_{H_2}$ = 50 mm

Ruthenium acetate and its adducts with triphenyl phosphine and pyridine may be prepared as described in Example 10.

EXAMPLE 4

Molybdenum system

Activity of protonated $Mo_2(COOCH_3)_4$ in the hydrogenation of hex-1-ene was as follows:

[Mo] = 0.015 M
[Hex-1-ene] = 1 M  $P'_{H_2}$ = 40 cm  Reaction temperature 35°
Rate = 0.32 ml/min.

EXAMPLE 5

Hydroformylation

Solutions with $Rh:PPH_3$ of 1:2 were found to be active for hydroformylation reactions.

$Rh_2(OCOCH_3)_4 + 4HBF_4 + 4PPh_3$ in methanol (corresponding to 5 mM metal concentration) containing substrate hex-1-ene (1M) was treated with $CO + H_2$ (1:1) at 35°C and either 45 cm or 1 atm pressure. After 15 hours the formation of heptaldehydes was confirmed by g.l.c. The rate was increased at higher pressures and temperatures.

EXAMPLE 6

Acetic Acid synthesis

A 1:2 ratio of $Rh:PPh_3$ is also effective for the carbonylation of methanol to acetic acid and methyl acetate, $Rh_2(OCOCH_3)_4 + 4HBF_4 + 4PPh_3$ in methanol (ca. 2.5 mM metal concentration was treated with CO at 100°/50 atm. pressure in presence of a trace of methyl iodine. The formation of acetic acid was detected by g.l.c. Using 5 ml. of a 0.02 M $Rh_2^{4+}$ solution and 45 mls methanol the reaction occurred at 100°C and 25 atm. CO.

EXAMPLE 7

Heterogeneous Catalysis a. A 2 g sample of "Dowex" (a registered trade mark of the Dow Chemical Company) 50W-X8 cation exchange resin (20–50 MS mesh H form) was allowed to absorb the protonated aqueous fluoroboric acid (2M) solution of rhodium (II) acetate (0.1 g). The now green resin was washed with methanol and then treated with a methanol solution saturated with triphenyl-phosphine which turned the resin red. The resin catalyst thus prepared was suspended in methanol (50 ml) and hex-1-ene (6 ml, 1M) was added. At 50 cm hydrogen pressure the rate of uptake at 20°C was found to be 10 ml. min.$^{-1}$.

b. 15 ml of resin, prepared as in (a), holding Rh equivalent to a 10 mM solution at $P_{H_2}$ = 45 cm, [$PPh_3$] = 5 mM, reaction temperature = 25°C, gave a rate for 1 M hex-1-ene of 1 ml.min.$^{-1}$.

EXAMPLE 8

The stoichiometric protonation by $HBF_4$ in methanol of the benzoate complex $Rh_2(OCOPh)_4.2PPh_3$ gives a brown-green solution which is also comparable in activity to the protonated acetate.

Thus, for hex-1-ene under the standard conditions of Example 2 but with [Rh] = 1.25 mM and with no added phosphine the rate of hydrogen uptake was 4.4 ml. min$^{-1}$.

The benzoate complex itself may be obtained in a manner similar to that of the acetate, i.e. with benzoic acid and sodium benzoate instead of acetic acid and sodium acetate.

Bis (triphenyl phosphine) and bis (pyridine) adducts may also be obtained with the benzoate complex.

EXAMPLE 9

The table below gives data for the hydrogenation of hex-1-ene obtained at 30°C using the $Rh_2^{4+}/PPh_3$ catalyst under a range of catalytic conditions. These results indicate the dependence of the rate of hydrogenation as a function of [Rh,] [hex-1-ene], and $H_2$ pressure ($P_{H_2}$).

Although at the lower concentration of rhodium, hexene and $H_2$, the observed rates show approximately first order dependence on each of these concentration variables, the rate dependencies deviate markedly from linearity at the higher concentrations. This would seem to suggest that a number of complex equilibria may be involved. As noted earlier, the ratio of $Rh:PPh_3$ of 1:2 is the most favourable and was used throughout. Rates of hydrogenation of hex-1-ene at 30°C using the $Rh_2^{4+}/PPh_3$ catalyst under a range of conditions.

| [Rh] mM | $P_{H_2}$ mm | [Hex-1-ene] M | [$PPh_3$] mM | Rate × 10$^4$ M.sec.$^{-1}$ |
|---|---|---|---|---|
| 1.0 | 400 | 1.0 | 2.0 | 1.10 |
| 2.0 |  |  | 4.0 | 2.19 |
| 3.0 |  |  | 6.0 | 2.96 |
| 4.0 |  |  | 8.0 | 3.48 |
| 2.0 | 400 | 0.5 | 4.0 | 1.23 |
|  |  | 1.5 |  | 2.98 |
|  |  | 2.0 |  | 3.38 |
|  |  | 3.0 |  | 3.58 |
| 2.0 | 150 | 1.0 | 4.0 | 1.62 |
|  | 200 |  |  | 1.66 |
|  | 300 |  |  | 1.80 |
|  | 350 |  |  | 1.88 |

EXAMPLE 10

Protonation of $Ru_2(OCOMe)_4Cl$ and $Ru_2 (OCOMe)_4$.

The chloroacetate is readily protonated by fluoroboric acid in methanol at 60°C under conditions similar to those used for rhodium (II) acetate. The final solution is deep blue and extremely air sensitive, turning first green on exposure to air and finally yellow-brown. The blue solution is readily absorbed on to a cation exchange resin (H form) and the eluate can be shown to contain acetic acid, as in the rhodium case. The electronic absorption spectrum of the aqueous protonated solution. λ max (E) 437 (460), 537 sh (180), is different from that of the aqueous solution of $Ru_2$ (OCOMe)$_4$Cl, 423 (750). The exact nature of the cationic species is not certain at present.

Although the blue solutions are not catalytically active under mild conditions, again like the rhodium system, the addition of a stabilising donor or biphyllic ligand such as triphenyl phosphine immediately gives a very active catalyst for the hydrogenation of alkenes and alkynes (see Example 3) without causing any initial colour change. Under hydrogen the blue solution becomes a more greenish blue and, as the hydrogenation of alkene proceeds, the solution becomes mauve.

The protonated adduct $Ru_2(OCOMe)_4.2PPh_3$ in the presence of excess triphenyl phosphine produced a catalytic species that catalysed the hydrogenation of hex-1-ene. (See example 3A).

Green ruthenium (II) acetate. $Ru_2(OCOMe)_4$ is obtained by the interaction of commercial ruthenium trichloride with acetic acid, sodium acetate and ethanol under reflux. It is difficult to obtain the acetate entirely free of sodium acetate and solvent, but it can be readily isolated as its green triphenyl phosphine adduct $Ru_2(OCOMe)_4.2PPh_2$. The acetate and its adduct are both diamagnetic (n.m.r.) The bis(pyridine) adducts is similarly isolatable as dark blue crystals.

A very low rate of hydrogenation was observed when using the protonated adduct in excess triphenyl phosphine for cis-pent-2-ene and other internal alkenes such as cyclohexene. From this point of view the ruthenium catalyst appeared to be much more selective than the corresponding rhodium phosphine catalyst.

Selectivity was also observed between cyclic nonconjugated dienes, cyclo octa - 1,5 diene being hydrogenated very rapidly in contrast to a much slower rate for bicycle (2.2.1) hepta-2,5 diene.

What is claimed is:

1. A process for the homogeneous liquid phase hydrogenation of an olefinically or acetylenically unsaturated hydrocarbon to produce a hydrocarbon having a lower degree of unsaturation by contact of the said starting hydrocarbon with molecular hydrogen in the presence of a catalyst solution containing a catalytically effective amount of a cation selected from the group consisting of:

$M_2^{n+}$
$M_2(OCOR)_{4-n}{}^{n+}$
$M_2(OCSR)_{4-n}{}^{n+}$
and
$M2(SCSR)_{4-n}{}^{n+}$ the said solution being prepared by the addition of strong acid to a solution of a compound selected from the group consisting of $M_2(OCOR)_4$
$M_2(OCOR)_4L$
$M_2(OCOR)_4L_2$
$M_2(OCSR)_4$
$M_2(OCSR)_4L$
$M_2(OCSR)_4L_2$
$M_2(SCSR)_4$
$M_2(SCSR)_4L$
and
$M_2(SCSR)_4L_2$ where M is a metal selected from the group consisting of Mo, Cr, Cu, Re and metals of the platinum group;

R is selected from the group consisting of methyl and phenyl;

L is a ligand selected from the group consisting of $H_2O$, $CH_3OH$, $C_2H_5OH$, pyridine, $Cl^-$ and $Br^-$;

n is a positive integer from 1 to 4;

(OCOR) represents a carboxylate radical;

(OCSR) represents a thiocarboxylate radical, and (SCSR) represents a diethiocarboxylate radical, and the said solution including a stabilising amount of a donor ligand selected from the group consisting of pyridine, quinoline, dimethylaniline, dibutyl sulphide, dimethyl sulphoxide, triphenyl phosphine oxide, phenyl isocyanide, acetonitrile, phosphorus tri-isocyanate, phosphorus triisothiocyanate, stannous halide, germanium (II) halide and a ligand having the formula $MR'_3$ where M is selected from the group consisting of phosphorus, arsenic and antimony and the R' substituents, which may be the same or different, are selected from the group consisting of alkyl and aryl radicals.

2. A process according to claim 1 in which R' is selected from the group consisting of methyl, ethyl, butyl and phenyl radicals.

3. A process according to claim 1 in which $MR_3'$ is selected from the group consisting of tributyl phosphine, triphenyl phosphine, ethyl diphenyl phosphine, dimethyl phenyl arsine, triphenyl-arsine and triphenyl stibine.

4. A process according to claim 1 in which the metal of the platinum group is selected from the group consisting of rhodium and ruthenium.

5. A process according to claim 4 in which a platinum group metal and triphenylphosphine are present in the approximate ratio of 1:2.

6. A process according to claim 1 in which the strong acid is selected from the group consisting of fluoroboric acid, perchloric acid, fluorosulphuric acid, trifluoromethane sulphuric acid, sulphuric acid, hydrofluoric acid and hyrdofluoric acid in combination with a Lewis acid.

7. A process according to claim 6 in which the Lewis acid is selected from the group consisting of a $SbF_5$, $SiF_4$ and $BF_3$.

8. A process according to claim 1 in which $M_2(OCOR)_4$ is selected from the group consisting of:

$Rh_2(OCOCH_3)_4$
$Mo_2(OCOCH_3)_4$
$Cr_2(OCOCH_3)_4$
$Ru_2(OCOCH_3)_4$
$Cu_2(OCOCH_3)_4$
$Re_2(OCOCH_3)_4$
and
$Ir_2(OCOCH_3)_4$.

9. A process according to claim 1 in which $M_2(OCOR)_4L$ is $Ru_2(OCOCH_3)_4Cl$.

10. A process according to claim 1 in which $M_2(OCOR)L_2$ is selected from the group consisting of $Re_2(OCOCH_3)_4Cl_2$
and
$Re_2(OCOCH_3)_4(CO)_2$.

11. A process according to claim 1 in which $M_2(OCSR)_4$ is selected from the group consisting of $Rh_2(OCSCH_3)_4$
$Mo_2(OCSCH_3)_4$
$Cr_2(OCSCH_3)_4$
$Ru_2(OCSCH_3)_4$
$Cu_2(OCSCH_3)_4$
$Re_2(OCSCH_3)_4$
and
$Ir_2(OCSCH_3)_4$.

12. A process according to claim 1 in which $M_2(OCSR)_4L$ is $Ru_2(OCSCH_3)_4Cl$.

13. A process according to claim 1 in which $M_2(OCSR)L_2$ is selected from the group consisting of $Re_2(OCSCH_3)_4Cl_2$
and
$Re_2(OCSCH_3)_4(CO)_2$.

14. A process according to claim 1 in which $M_2(SCSR)_4$ is selected from the group consisting of $Rh_2(SCSCH_3)_4$
$Mo_2(SCSCH_3)_4$
$Cr_2(SCSCH_3)_4$
$Ru_2(SCSCH_3)_4$
$Cu_2(SCSCH_3)_4$
$Re_2(SCSCH_3)_4$
and
$Ir_2(SCSCH_3)_4$.

15. A process according to claim 1 in which $M_2(SCSR)_4L$ is $Ru_2(SCSCH_3)_4Cl$.

16. A process according to claim 1 in which $M_2(SCSR)_4L_2$ is selected from the group consisting of $Re_2(SCSR)_4Cl_2$ and $Re_2(SCSR)_4(CO)_2$.

17. A process for the hydrogenation of an olefinically or acetylinically unsaturated hydrocarbon to produce a hydrocarbon having a lower degree of unsaturation by contact of the said starting hydrocarbon with molecular hydrogen in the presence of a heterogeneous catalyst composition consisting essentially of a cation exchange solid having exchanged on to it a cation selected from the group consisting of $M_2^{n+}$ $M_2(OCOR)_{4-n}^{n+}$ $M_2(OCSR)_{4-n}^{n+}$ and $M_2(SCSR)_{4-n}^{n+}$ by passage through it of a solution according to claim 1.

18. A process according to claim 17 in which the cation exchange solid is selected from the group consisting of cation exchange resins, zeolites and phosphates.

19. A process according to claim 18 in which the cation exchange resin is in the form of porous sulphonated polystyrene resin beads.

20. A process according to claim 18 in which the phosphate is sodium hexametaphosphate.

21. A process according to claim 1 in which the catalyst solution is adsorbed on to activated charcoal.

22. A process for the homogeneous liquid phase hydrogenation of an olefinically or acetylenically unsaturated hydrocarbon to produce a hydrocarbon having a lower degree of unsaturation by contact of the said starting hydrocarbon with molecular hydrogen in the presence of a catalyst solution containing a catalytically effective amount of a cation selected from the group consisting of:

$M_2^{n+}$ $M_2(OCOR)_{4-n}^{n+}$ $M_2(OCSR)_{4-n}^{n+}$ and $M_2(SCSR)_{4-n}^{n+}$ the said solution being prepared by the addition of strong acid to a solution of a compound selected from the group consisting of $M_2(OCOR)_4$ $M_2(OCOR)_4L$ $M_2(OCOR)_4L_2$ $M_2(OCSR)_4$ $M_2(OCSR)_4L$ $M_2(OCSR)_4L_2$ $M_2(SCSR)_4$ $M_2(SCSR)_4L$ and $M_2(SCSR)_4L_2$ where M is a metal selected from the group consisting of Mo, Cr, Cu, Re and metals of the platinum group;

R is selected from the group consisting of alkyl and aryl;

L is a ligand selected from the group consisting of $H_2O$, $CH_3OH$, $C_2H_5OH$, CO, pyridine, $Cl^-$ and $Br^-$;

$n$ is a positive integer from 1 to 4;

(OCOR) represents a carboxylate radical;

(OCSR) represents a thiocarboxylate radical, and (SCSR) represents a dithiocarboxylate radical, and the said solution including a stabilising amount of a donor ligand selected from the group consisting of pyridine, quinoline, dimethylaniline, tributylphosphine, triphenylphosphine, dimethylphenylarsine, triphenylarsine, triphenylstibine, dibutyl sulphide, dimethyl sulphoxide, triphenyl phosphine oxide, phenyl isocyanide, acetonitrile, phosphorus tri-isocyanate, phosphorus tri-isethiocyanate, stannous halide and germanium (II) halide.

* * * * *